(12) United States Patent
White et al.

(10) Patent No.: US 8,536,256 B2
(45) Date of Patent: Sep. 17, 2013

(54) DOPO-DERIVED FLAME RETARDANT AND EPOXY RESIN COMPOSITION

(75) Inventors: Kimberly M. White, Baton Rouge, LA (US); Yu Li Angell, Pasadena, TX (US); Scott E. Angell, Pasadena, TX (US); Arthur G. Mack, Prairieville, LA (US)

(73) Assignee: Albemarle Corporation, Baton Rouge, LA (US)

( * ) Notice: Subject to any disclaimer, the term of this patent is extended or adjusted under 35 U.S.C. 154(b) by 0 days.

(21) Appl. No.: 13/319,486

(22) PCT Filed: May 19, 2010

(86) PCT No.: PCT/US2010/035354
§ 371 (c)(1),
(2), (4) Date: Nov. 8, 2011

(87) PCT Pub. No.: WO2010/135393
PCT Pub. Date: Nov. 25, 2010

(65) Prior Publication Data
US 2012/0055705 A1 Mar. 8, 2012

Related U.S. Application Data

(60) Provisional application No. 61/179,510, filed on May 19, 2009.

(51) Int. Cl.
*C08K 5/51* (2006.01)

(52) U.S. Cl.
USPC .......................................... 524/119; 524/710

(58) Field of Classification Search
USPC .................................................. 524/119, 710
See application file for complete search history.

(56) References Cited

U.S. PATENT DOCUMENTS 6,441,067 B1 8/2002 Chiu et al.
2006/0247344 A1 11/2006 Mueller et al.

FOREIGN PATENT DOCUMENTS

| JP | 11106619 A | 4/1999 |
| JP | 2001270993 A | 10/2001 |
| JP | 2002193985 A | 7/2002 |
| WO | 2008119693 A1 | 10/2008 |

OTHER PUBLICATIONS

XP-008099832; Johannes Artner, et al; "A Novel and Effective Synthetic Approach to 9,10-Dihydro-9-oxa-10-phosphaphenanthrene-10-oxide (DOPO) Derivatives"; Phosphorus, Sulfur, and Silicon; 2007; p. 2131-2148; vol. 182; No. 9; Taylor & Francis Group, LLC; US.
XP-002499618; Edward D. Weil; "Flame Retardants, Phosphorus"; Kirk-Othmer Encyclopedia of Chemical Technology; pp. 484-510; vol. 11; Online—Posted Dec. 4, 2000; John Wiley & Sons, Inc.; US.

*Primary Examiner* — Kriellion Sanders
(74) *Attorney, Agent, or Firm* — James A. Jubinsky; Marcy M. Hoefling; Nathan C. Dunn

(57) ABSTRACT

This invention relates to 9,10-Dihydro-9-Oxa-10-Phosphaphenantrene-10-oxide derived additive flame-retardants, which are useful in epoxy resin compositions. The epoxy resin compositions may be used in making prepregs or laminates for printed wiring boards and composite materials.

15 Claims, No Drawings

DOPO-DERIVED FLAME RETARDANT AND EPOXY RESIN COMPOSITION

TECHNICAL FIELD

This invention relates to 9,10-Dihydro-9-Oxa-10-Phosphaphenantrene-10-oxide derived additive flame-retardants, which are useful in epoxy resin compositions. The epoxy resin compositions may be used in making prepregs or laminates for printed wiring boards and composite materials.

BACKGROUND

Epoxy resins are employed for a wide range of applications such as electronic components, electrical equipment, automotive parts and sporting equipment since the epoxy resins have desirable properties such as adhesiveness, heat resistance and moldability. Flame-retardant agents, in particular brominated epoxy resins compounds are employed for copper-clad laminates and sealants that are used in electronic components and electrical equipment. However, halogen-containing compounds cause concerns about environment and human safety, and therefore flame-retardant agents that are more environmentally friendly are desirable.

Types of flame retardants that are perceived to be more environmentally friendly include organo-phosphorous flame retardants. In the field of epoxy resins and laminates, organo-phosphorous flame retardants with reactive groups, such as those derived from 9,10-Dihydro-9-Oxa-10-Phosphaphenantrene-10-oxide (DOPO), are typically used in epoxy resin formulations because they react with the epoxy to form a phosphorus-modified epoxy resin. The technology for producing phosphorus-modified epoxy resins and their uses, including their use in forming prepregs, laminates and copper-clad laminates is well known in the art. See for example U.S. Pat. Nos. 5,036,135; 5,364,893; 5,376,453; 5,587,243; 5,759,690; 5,817,736, 6,291,626 B1; 6,291,627 B1; 6,296,940 B1; 6,353,080 B1; 6,403,220 B1; 6,403,690 B1; 6,486,242 B1; and WO 01/42359 A1 as published in English on Jun. 14, 2001.

However, "additive" organophosphorus flame retardants, which do not have reactive groups, are typically not used in epoxy formulations, since it is believed that covalent bonding between the epoxy resin and a reactive organophosphorus flame retardant are needed to provide high glass transition temperatures and dimensional stability. The present invention relates to the use of additive flame-retardants derived from DOPO and their use in epoxy resin formulations.

SUMMARY OF THE INVENTION

The present invention relates to a flame retardant epoxy composition comprising:
an epoxy compound;
(ii) a compound having the following structure:

Formula I

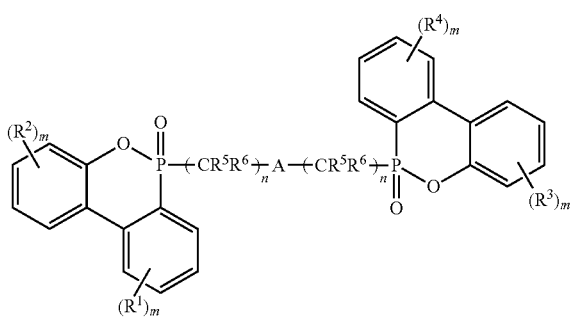

wherein A is a direct bond, $C_6$-$C_{12}$ aryl, $C_3$-$C_{12}$ cycloalkyl, or a $C_3$-$C_{12}$ cycloalkenyl, wherein said cycloalkyl or cycloalkenyl may be optionally substituted by a $C_1$-$C_6$ alkyl; each $R^1$, $R^2$, $R^3$ and $R^4$ are independently hydrogen, $C_1$-$C_{15}$ alkyl, $C_6$-$C_{12}$ aryl, $C_7$-$C_{15}$ aralkyl alkaryl; or $R^1$ and $R^2$ or $R^3$ and $R^4$ taken together can form a saturated or unsaturated cyclic ring, wherein said saturated or unsaturated cyclic ring may be optional substituted by a $C_1$-$C_6$ alkyl; each m is independently 1, 2, 3 or 4; each $R^5$ and $R^6$ are independently hydrogen or a $C_1$-$C_6$ alkyl; and each n is independently 0, 1, 2, 3, 4 or 5; with the proviso that when A is aryl or a direct bond, n can not be 0.

DETAILED DESCRIPTION OF THE INVENTION

The present invention relates to a flame retardant epoxy composition comprising:
(i) an epoxy compound;
(ii) a compound having the following structure:

Formula I

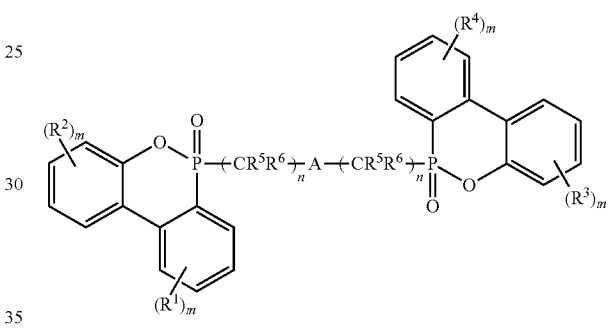

wherein A is a direct bond, $C_6$-$C_{12}$ aryl, $C_3$-$C_{12}$ cycloalkyl, or a $C_3$-$C_{12}$ cycloalkenyl, wherein said cycloalkyl or cycloalkenyl may be optional substituted by a $C_1$-$C_6$ alkyl; each $R^1$, $R^2$, $R^3$ and $R^4$ are independently hydrogen, $C_1$-$C_{15}$ alkyl, $C_6$-$C_{12}$ aryl, $C_7$-$C_{15}$ aralkyl or $C_7$-$C_{15}$ alkaryl; or $R^1$ and $R^2$ or $R^3$ and $R^4$ taken together can form a saturated or unsaturated cyclic ring, wherein said saturated or unsaturated cyclic ring may be optional substituted by a $C_1$-$C_6$ alkyl; each m is independently 1, 2, 3 or 4; each $R^5$ and $R^6$ are independently hydrogen or a $C_1$-$C_6$ alkyl; and each n is independently 0, 1, 2, 3, 4 or 5; with the proviso that when A is aryl or a direct bond, n can not be 0.

In one aspect, both n subscripts are 1 or 2 and A is a direct bond. In another aspect, both n subscripts are 1 and A is a $C_6$-$C_{12}$ aryl. In another aspect, $R^1$, $R^2$, $R^3$ and $R^4$ are independently hydrogen or a $C_1$-$C_6$ alkyl. In another aspect, $R^5$ and $R^6$ are each independently hydrogen or methyl.

Specific compounds of Formula I that may be used in this invention are 6H-ibenz[c,e][1,2]oxaphosphorin, 6,6'-(1,4-ethanediyl)bis-, 6,6'-dioxide; 6H-Dibenz[c,e][1,2]oxaphosphorin, 6,6'-(1,4-butanediyl)bis-, 6,6'-dioxide; or 6H-Dibenz[c,e][1,2]oxaphosphorin, 6,6'-(p-xylenediyl)bis-, 6,6'-dioxide.

The term "alkyl", as used herein, unless otherwise indicated, includes saturated monovalent hydrocarbon radicals having straight or branched moieties. Examples of alkyl groups include, but are not limited to, methyl, ethyl, propyl, isopropyl, butyl, isobutyl, t-butyl, pentyl and hexyl.

The term "aryl", as used herein, unless otherwise indicated, includes an organic radical derived from an aromatic hydrocarbon by removal of one hydrogen, such as phenyl, naphthyl, indenyl, and fluorenyl. "Aryl" encompasses fused ring groups wherein at least one ring is aromatic.

The term "aralkyl" as used herein indicates an "aryl-alkyl-" group. Non-limiting example of an aralkyl group is benzyl ($C_6H_5CH_2$—) and methylbenzyl ($CH_3C_6H_4CH_2$—).

The term "alkaryl" as used herein indicates an "alkyl-aryl-" group. Non-limiting examples of alkaryl are methylphenyl-, dimethylphenyl-, ethylphenyl-propylphenyl-, isopropylphenyl-, butylphenyl-, isobutylphenyl- and t-butylphenyl-.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl.

The term "cycloalkenyl", as used herein, unless otherwise indicated, includes non-aromatic cyclic alkenyl moieties wherein alkenyl is as defined above. Examples of cycloalkyl include, but are not limited to, cyclopropenyl, cyclobutenyl, cyclopentenyl, cyclohexenyl, and cycloheptenyl.

Unless otherwise indicated, all the foregoing groups derived from hydrocarbons may have up to about 1 to about 20 carbon atoms (e.g., $C_1$-$C_{20}$ alkyl, $C_6$-$C_{20}$ aryl, $C_7$-$C_{20}$ alkaryl, $C_7$-$C_{20}$ aralkyl) or 1 to about 12 carbon atoms (e.g., $C_1$-$C_{12}$ alkyl, $C_6$-$C_{12}$ aryl, $C_7$-$C_{12}$ alkaryl, $C_7$-$C_{12}$ aralkyl), or 1 to about 8 carbon atoms, or 1 to about 6 carbon atoms.

Any suitable epoxy resin useful in the art may be used in the present invention as the epoxy compound. Representative epoxy resins suitable for use in the present invention are presented in Epoxy Resins Chemistry and Technology, Second Edition edited by Clayton A. May (Marcel Dekker, Inc. New York, 1988), Chemistry and Technology of Epoxy Resins edited by B. Ellis (Blackie Academic & Professional, Glasgow, 1993), Handbook of Epoxy Resins by H. E. Lee and K. Neville (McGraw Hill, New York, 1967.

It is generally advantageous to use an epoxy resin, which possesses an average functionality more than 1 and preferably at least 1.8, more preferably at least 2 epoxy groups per molecule. In the more preferred case, the epoxy resin is a novolac epoxy resin with at least 2.5 epoxy groups per molecule. In another aspect of the invention, the epoxy resin may be any saturated or unsaturated aliphatic, cycloaliphatic, aromatic or heterocyclic compound, which possesses more than one 1.2-epoxy groups. Examples of heterocyclic epoxy compounds are diglycidylhydantoin or triglycidyl isocyanurate (TGIC).

Suitable epoxy resins are, but not limited to, epoxy resins based on bisphenols and polyphenols, such as, bisphenol A, tetramethylbisphenol A, bisphenol F, bisphenol S, tetrakisphenylolethane, polybenzoxazine, resorcinol, 4,4'-biphenyl, dihydroxynaphthylene, and epoxy resins derived from novolacs, such as, phenol:formaldehyde novolac, cresol:formaldehyde novolac, bisphenol A novolac, biphenyl-, toluene-, xylene, or mesitylene-modified phenol:formaldehyde novolac, aminotriazine novolac resins and heterocyclic epoxy resins derived from p-amino phenol and cyanuric acid. Additionally, aliphatic epoxy resins derived from 1,4-butanediol, glycerol, and dicyclopentadiene skeletons, are suitable, for example. Many other suitable epoxy resin systems are available and would also be recognized as being suitable by one skilled in the art.

Epoxy novolac resins (including epoxy cresol novolac resins) are readily commercially available, for example, under the trade names D.E.N™, QUATREX.™ (Trademarks of the Dow Chemical Company), Tactix™ 742 (Trademarks of Ciba) and Epon™ (trademark of Resolution Performance Products). The materials of commerce generally comprise mixtures of various glycidoxyphenyl and methyl-, ethyl-propyl-glycidoxyphenyl groups.

In general, the amount of the compound of Formula I in the flame retardant epoxy composition is about 0.1 to about 100 parts, or about 1 to 70 parts, by weight per 100 parts by weight of the epoxy compound.

Alternatively, the amount of the phosphorus compound of Formula I in the flame retardant epoxy composition is selected so the composition will contain about 0.5 wt % to about 10 wt % or about 1.2 wt % to about 7 wt %, or about 1.5 wt % to about 5 wt % phosphorous content, based on the total weight of the composition.

The phosphorus-containing flame retardant epoxy composition has an epoxy equivalence of generally about 100 g/eq to about 1000 g/eq., or about 100 g/eq to about 800 g/eq or about 150 g/eq to about 500 g/eq.

The present invention also relates to a cured flamed retardant epoxy resin comprising the flame-retardant epoxy resin composition above reacted with a curing or polymer initiation agent.

The aforementioned curing or polymerization initializing agents are not limited to a specific curing or polymerization initializing agent as long as the agent helps polymerization of the epoxy resin in the flame retardant epoxy composition.

Examples of polymerization initializing agents are cationic polymerization initializing agents such as methane sulfonic acid, aluminum chloride, stannum chloride, trifluoroboron ethylamine complex, trifluoroboron ethylether complex and the like; radical polymerization initializing agents such as benzoyl peroxide, dicumyl peroxide, azo bis-isobutyronitrile and the like; and anionic polymerization initializing agents such as methoxy potassium, triethyl amine, 2-dimethyl aminophenol and the like and mixtures thereof.

The aforementioned epoxy curing agents include any agent known by a person skilled in the art. Examples, include but are not limited to: ethylene diamine, trimethylene diamine, tetramethylene diamine, hexamethylene diamine, meta phenylene diamine, para phenylene diamine, para xylene diamine, 4,4'-diamino diphenyl methane, 4,4'-diamino diphenyl propane, 4,4'-diamino diphenyl ether, 4,4'-diamino diphenyl sulfone, 4,4'-diamino dicyclohexane, bis (4-aminophenyl) phenyl methane, 1,5-diamino naphthalene, meta xylylene diamine, para xylylene diamine, 1,1-bis (4-aminophenyl) cyclohexane, dicyan diamide, phenol/formaldehyde novolac, cresol/formaldehyde novolac, bisphenol A novolac, biphenyl-, toluene-, xylene-, or mesitylene-modified phenol/formaldehyde novolac, aminotriazine novolac, cresol/formaldehyde/aminotriazine novolac, phenol/formaldehyde/aminotriazine novolac or mixtures thereof.

The amount of curing agent that may be used is based on the molar equivalence of curing functional groups in the curing agent to the molar equivalence of un-reacted epoxy groups in the flame-retardant epoxy resin composition. Thus, the curing agent amount may be from about 0.1 equivalence to about 10 equivalence or about 0.3 equivalence to about 5 equivalence, or about 0.7 equivalence to about 2 equivalence based on the equivalence of unreacted epoxy groups in the phosphorus-containing epoxy resin.

The polymerization initializing agents may be added in concentrations ranging from about 0.01 wt % to about 10 wt %, or about 0.05 to about 5%, or about 0.1 wt % to about 2 wt %, based on the total weight of the flame-retardant epoxy resin composition.

The curing temperature may be carried out generally between about 25° C. to about 250° C., or about 70° C. to about 240° C. or about 150° C. to about 220° C.

In addition, epoxy curing agent promoters may also be used to promote curing of the flame retardant epoxy composition. These epoxy curing agent promoter are often based on imidazoles. Examples of such epoxy curing agent promoters include, but are not limited to: 1-methylimidazole, 2-methylimidazole, 1,2-dimethylimidazole, 1,2,4,5-tetramethylimidazole, 2-ethyl-4-methylimidazole, 2-phenylimidazole, 1-cyanoethyl-2-phenylimidazole, 1-(4,6-diamino-s-triazinyl-2-ethyl)-2-phenylimidazole or mixtures thereof.

When phenol novolacs are used as curing agents, the epoxy curing agent promoter may be added in concentrations ranging from about 0.0001 wt % to about 5 wt %, or about 0.01 to about 3%, or about 0.1 wt % to about 2 wt %, or about 0.15 wt % to about 1 wt %, based on the weight of curing agent used. Higher concentrations of promoter may be used with different curing agents, such as DICY, dicyandiamide, where promoter concentrations are more typically in the 5-25 wt % range, based on weight of curing agent.

The aforementioned cured flamed retardant epoxy resin and/or flame-retardant epoxy compositions of the invention may also contain other conventional additives, such as heat stabilizers, light stabilizers, ultra-violet light absorbers, antioxidants, anti-static agents, preservatives, adhesion promoters, fillers, pigments, dyes, lubricants, mold releasers, blowing agents, fungicides, plasticizers, processing aids, acid scavengers, dyes, pigments, nucleating agents, wetting agents, dispersing agents, synergists, mineral fillers, reinforcing agents such as glass fiber, glass flake, carbon fiber, or metal fiber; whiskers such as potassium titanate, aluminum borate, or calcium silicate; inorganic fillers and other fire-retardant additives and smoke suppressants and mixtures thereof.

The other fire retardant additives which may be used with the compounds of formula I include, but are not limited to, ammonium polyphosphate, nitrogen-containing synergists such as melamine polyphosphate, antimony oxide, silica, hydrated alumina such as aluminum hydroxide (ATH), boehmite, bismuth oxide, molybdenum oxide, or mixtures of these compounds with zinc, aluminum and/or magnesium oxide or salts.

Inorganic fillers may be used in the invention to affect physical properties and to reduce costs. Typically, fillers and reinforcing agents include fused silica powder; crystalline silica powder; alumina; silicon nitride; aluminum nitride; boron nitride; magnesia; titanium oxide; calcium carbonate; magnesium carbonate; calcium silicate; glass fiber; asbestos, talc, kaolin, bentonite, wollastonite, glass fiber, glass fabrics, glass matt, milled glass fiber, glass beads (solid or hollow), silicon carbide whiskers and mixtures thereof Many of these materials are enumerated in the Encyclopedia of Materials Science and Engineering, Vol. #3, pp. 1745 1759, MIT Press, Cambridge, Mass. (1986), the disclosure of which is incorporated herein by reference. Combinations of fillers are preferred in some embodiments; whereas in other embodiments, the reinforcing agent makes up much of the composite of the invention, as in the case of glass fabric used in prepregs and laminates for printed wiring boards.

Preferably, the compound of formula I is grounded or milled prior to combining with the polymer. The $d_{50}$ particle size after grinding or milling may be less than about 15 µm, or less than 10 µm, or less than about 5 µm, or less than about 3 µm or less than about 2 µm. The $d_{50}$ particle size may even be less than 1 µm, such as about 100 nm to 800 nm. A particle size of $d_{50}$ is the median particle size, where half the particles are above the value and half the particles are below the value. Any suitable milling or grinding technique may be used such as jet milling.

It is also preferred that the compound of Formula I have a monomodal particle size distribution, preferably when the $d_{50}$ particle size is greater than about 2 µm so that the compound may be more homogenously blended with the polymer.

To determine median particle size, a Coulter LS-230 counter or equivalent is used with its small volume module. The operating instructions of the manufacturer are followed. Alternatively, a Horiba laser light scattering instrument (e.g., Horiba LA900 Model 7991) or equivalent can be used. The procedure involves weighing the sample, typically an amount in the range of about 0.01 gram to about 0.015 gram, into a clean dry aluminum cup that has been washed with deionized water before use. The instrument autosampler disperses a 0.05 g sample in water using 0.4 mL of 1% Triton X-100 surfactant and ultrasonic treatment. This suspension is circulated through a measuring cell where the powder particles scatter a beam of laser light. Detectors in the instrument measure intensity of the light scattered. The computer in the instrument calculates mean particle size, average particle size and particle size distribution from such measurements.

The aforementioned cured flamed retardant epoxy resin and/or flame-retardant epoxy composition of the invention may be used to form prepreg and/or laminates. Typical procedures for forming prepregs and laminates for printed wiring boards involve such operations as:

A) An epoxy-containing formulation such as one containing the flame retardant epoxy composition of the present invention, is formulated with solvents and curing or polymerization agents and optionally other conventional additives described above. The formulation is applied to or impregnated into a substrate by rolling, dipping, spraying, other known techniques and/or combinations thereof. The substrate is an inorganic or organic reinforcing agent in the form of fibers, fleece, fabric, or textile material, e.g., typically a woven or non-woven fiber mat containing, for instance, glass fibers or paper.

B) The impregnated substrate is "B-staged" by heating at a temperature sufficient to draw off solvent in the epoxy formulation and optionally to partially cure the epoxy formulation, so that the impregnated substrate cooled to room temperature is dry to the touch and can be handled easily. The "B-staging" step is usually carried out at a temperature of from 90° C. to 240° C. and for a time of from 1 minute to 15 minutes. The impregnated substrate that results from B-staging is called a "prepreg." The temperature is most commonly 100° C. for composites and 130° C. to 200° C. for electrical laminates.

C) One or more sheets of prepreg are stacked or laid up in alternating layers with one or more sheets of a conductive material, such as copper foil, if an electrical laminate is desired.

D) The laid-up sheets are pressed at high temperature and pressure for a time sufficient to cure the resin and form a laminate. The temperature of this lamination step is usually between 100° C. and 240° C., and is most often between 165° C. and 200° C. The lamination step may also be carried out in two or more stages, such as a first stage between 100° C. and 150° C. and a second stage at between 165° C. and 200° C. The pressure is usually between 50 N/cm² and 500 N/cm². The lamination step is usually carried out for a time of from 1 minute to 200 minutes, and most often for 45 minutes to 120 minutes. The lamination step may optionally be carried out at higher temperatures for shorter times (such as in continuous lamination processes) or for longer times at lower temperatures (such as in low energy press processes).

E) Optionally, the resulting laminate, for example, a copper-clad laminate, may be post-treated by heating for a time at high temperature and ambient pressure. The temperature of post-treatment is usually between 120° C. and 250° C. The post-treatment usually is between 30 minutes and 12 hours.

F) Often an electrically-conductive printed circuit is applied to the copper-clad laminate. Typically, the solvent for the epoxy resin in step A above is a ketone such as 2-butanone or methyl ethyl ketone (MEK). However, any other suitable type of conventionally-used solvent for forming these formulations can be employed. Examples of such other solvents include, but are not limited to acetone, methyl isobutyl ketone (MIBK), 2-methoxy ethanol, 1-methoxy-2-propanol, propylene glycol monomethyl ether, ethylene glycol monoethyl ether acetate, toluene, N,N-dimethylformamide, and mixtures thereof.

Reaction Procedure

The present invention also relates to a process for making a compound having the following structure:

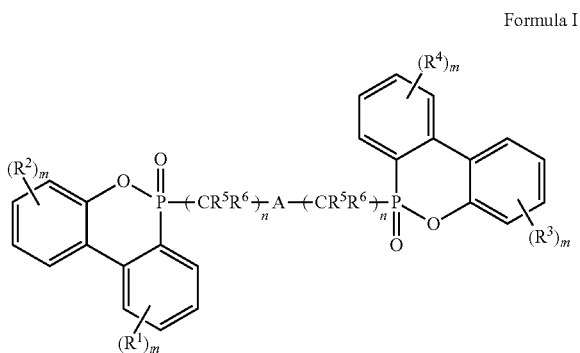

Formula I wherein A is a direct bond, $C_6$-$C_{12}$ aryl, $C_3$-$C_{12}$ cycloalkyl, or a $C_3$-$C_{12}$ cycloalkenyl, wherein said cycloalkyl or cycloalkenyl may be optional substituted by a $C_1$-$C_6$ alkyl; each $R^1$, $R^2$, $R^3$ and $R^4$ are independently hydrogen, $C_1$-$C_{15}$ alkyl, $C_6$-$C_{12}$ aryl, $C_7$-$C_{15}$ aralkyl or $C_7$-$C_{15}$ alkaryl; or $R^1$ and $R^2$ or $R^3$ and $R^4$ taken together can form a saturated or unsaturated cyclic ring, wherein said saturated or unsaturated cyclic ring may be optional substituted by a $C_1$-$C_6$ alkyl; each m is independently 1, 2, 3 or 4; each $R^5$ and $R^6$ are independently hydrogen or a $C_1$-$C_6$ alkyl; and each n is independently 0, 1, 2, 3, 4 or 5; with the proviso that when A is aryl or a direct bond, n can not be 0; comprising reacting a compound of Formula A

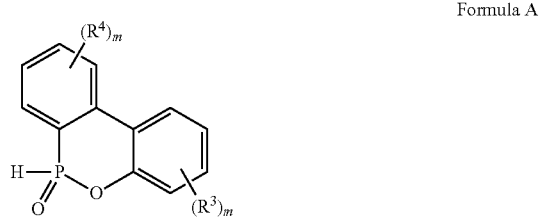

Formula A wherein $R^3$, $R^4$ and m are defined above;

with a compound of Formula B in the presence of a base;

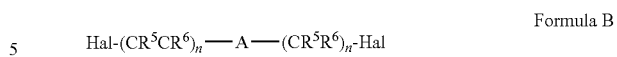

Formula B wherein $R^5$, $R^6$ and n are defined above and Hal is a halogen (e.g., F, Cl, I or Br); with the proviso that when A is aryl or a direct bond, n can not be 0.

One base that may be used is an alkali metal base such as alkali metal alkoxides, alkali metal amides and alkali metal alkyl amides. Alkali metals for the base include lithium, sodium and potassium. Examples of the bases that may be used include, but are not limited to, potassium methoxide, sodium methoxide, lithium methoxide, potassium ethoxide, sodium ethoxide, lithium ethoxide, potassium t-butoxide, sodium t-butoxide, lithium diisopropyl amide and mixtures thereof. Preferred are potassium t-butoxide and sodium methoxide.

Any suitable amount of base may be used in the process of this invention. Such suitable amounts include from about 0.1 to about 10 equivalences, or about 0.5 to about 5 equivalences, based on the amount of the compound of Formula A.

The process may also contain an optional solvent. Examples of such solvents may include, but are not limited to, heptane, hexane, petroleum ether, methylcyclohexane; toluene, xylene, ethyl benzene, tetrahydrofuran, dimethyl sulfoxide (DMSO), 1,4-dioxane, dimethyl formamide (DMF), dimethylacetamide (DMAc), acetonitrile, ethylene glycol dimethyl ether, ethylene glycol diethyl ether or mixtures thereof.

The process may be conducted at temperatures ranging from about −10° C. to about 75° C.

Another process used to produce the above compounds of Formula I may be found in U.S. Provisional Application No. 61/319,580, entitled Process for the Preparation of DOPO-Derived Compounds, filed on Mar. 31, 2010, herein incorporated by reference in its entirety. In that process, DOPO is reacted with ethylene glycol, in the presence of a catalyst at temperatures ranging from about 100° C. to about 250° C. The catalyst that may be used is any suitable catalyst for dehydration and/or Arbuzov reactions. General suitable catalysts are, alky halides, alkali halides, alkaline earth metal halides, transition metals and their halides or acid catalysts such as methyl p-toluenesulfonate, ethyl p-toluenesulfuonate. Arbuzov reaction catalysts are especially suitable. The process may optionally use a solvent, preferably a high boiling point solvent and an optional entrainer.

It is preferred that the purity of the compounds of Formula I, when combined with epoxies should be greater than about 95%, or about 98% or about 99%. The purity levels can be measured by using NMR spectroscopy. One skilled in the art of NMR spectroscopy can develop a procedure for measuring the purity of the compound of Formula I.

One NMR spectroscopy procedure that may be used to measure the purity of the compound of Formula I is discussed below. This procedure is suitable for the determination of purity by weight percent normalization versus observed impurities. This procedure is suitable for Formula I samples that can be completely dissolved in chloroform. Alternatively, if insoluble material is present, the purity of the sample may be assayed by 1H-NMR spectroscopy or 31P-NMR spectroscopy versus an internal standard such as trimethylphosphate. If an internal standard is used, assure that adequate prepulse delays are used to allow all nuclei of interest to return to equilibrium before further RF pulses.

Sample Prep:

Sample may be prepared on lab bench top by transferring about 500 mg of sample into a clean glass vial. It is unnecessary to record weight of sample. Add ~1-2 mL of CDCl$_3$ (>98% D) containing tetramethylsilane (TMS) to the vial. Cap and shake sample on vortex shaker until sample is completely dissolved. Transfer about 1 mL of above solution to a clean, dry 5 mm NMR tube. Acquire a $^1$H NMR spectrum using an inverse gated $^{13}$C decoupling experiment. The following parameters are suitable for detection of impurities present at about 100 ppm levels and higher:

Acquisition Parameters:

Nucleus: 1H; Pulse program: zgig30; Collected data points (TD): 64 k; Spectral Width (SWH): ~7000 Hz; Pre-pulse delay (D1): 60 sec minimum (use adequate prepulse delay to ensure all observed nuclei have adequate relaxation time); Acquisitions (NS): 4 scans minimum (enough scans to provide good signal to noise); Lock Solvent: CDCl3.

Process, using the efp command as a shortcut to perform the following: em (exponential multiplication window function,) ft (Fourier transform,) and pk (phase correction.) Manually phase correct the spectrum if necessary. Calibrate the chemical shift of the TMS peak to 0.0 ppm. The following processing parameters are suitable: SI: 64 k; Line broadening (LB): 0.2 Hz Integrate the following peaks in the $^1$H-NMR spectrum, paying careful attention to the slope and bias of each integral:

Formula I compound [mulitplet, ~8.2 to ~7.6 ppm, 8H, H—Ar], FW=458.4 g/mol

DOPO [singlet, ~8.6 ppm, 0.5; H, H—P, FW=216.2 g/mol

Para-xylene solvent [singlet, ~7.1 ppm, 4H, H—Ar], FW=106.2 g/mol

Ethylene glycol [singlet, ~3.6 ppm, 4H, H$_2$CO], FW=62.1 g/mol

Isopropyl alcohol (IPA) [doublet, ~1.2 ppm, 6H, H$_3$C—C], FW=60.1 g/mol

Spectral Interpretation and Calculations:

Formula I compound $^1$H-NMR spectrum consists of the following peaks: series of multiplets from ~8.0 ppm to ~7.2 ppm representing 16 aromatic protons and a multiplet centered @~2.4 ppm representing the four protons of the ethylene bridge.

A normalized wt % of each component using the following formula:

Wt % of component=($A1/B1*C1$)*100/Σ[($A1/B1*C1$)+($A2/B2*C2$)+ . . . ]

A=Area of component peak
B=# Nuclei represented by component peak
C=MW of component It is preferred that the compound of Formula I is substantially or completely free of organic bases because organic bases may deleteriously affect its use as a flame retardant, especially when used in epoxies. Substantially free of organic bases means that the levels are less than about 10,000 ppm, or less than about 1000 ppm, or less than about 100 ppm or less than about 10 ppm. One method to have the compound of Formula I be substantially or completely free of an organic base is not to use the any organic base in the reaction to produce the compound. One method to determine the amount of organic base, if any, is NMR spectroscopy.

An organic base is an organic compound, which acts as a base. Organic bases are usually, but not always, proton acceptors. They usually contain nitrogen atoms, which can be readily protonated. Amines and nitrogen-containing heterocyclic compounds are typically organic bases. Examples include, but are not limited to pyridine, methyl amine, trimethylamine, triethylamine, tripropylamine, tributylamine, N-ethylmorpholine, imidazole, benzimidazole, histidine, phosphazene bases and carbonates or hydroxides of some organic cations.

It is preferred that the compound of Formula I is substantially free of unreacted DOPO because DOPO may deleteriously affect its use as a flame retardant. Substantially free of DOPO means that the levels are less than about 50,000 ppm, or less than about 20,000 ppm, or less than about 10,000 ppm or less than about 1000 ppm or less than about 100 ppm. A preferred method to reduce the DOPO is to wash the product with water or water miscible solvents such as alcohols (e.g., isopropanol), aldehydes or ketones (e.g., acetone) before and/or after filtration. DOPO levels may be measured by using NMR spectroscopy.

It is preferred that the amount of solvent remaining in the compound of Formula I after purification should be less than about 1000 ppm, or less than about 100 ppm, or less than about 50 ppm. The amount of solvent may be measured by using NMR spectroscopy.

One method to reduce the amount of solvent in the compound of Formula I is drying under vacuum or with nitrogen sweep at temperature from about 100° C. to 170° C. for about 2 to about 24 hours. If the compound is grounded or milled, it is preferred to do at temperatures above room temperature, such as by hot air jet milling to further reduce volatiles.

The following Examples illustrate the present invention. It is to be understood, however, that the invention, as fully described herein and as recited in the Claims, is not intended to be limited by the details of the following Examples.

Example 1

6H-Dibenz[c,e][1,2]oxaphosphorin, 6,6'-(1,4-ethanediyl)bis-, 6,6'-dioxide

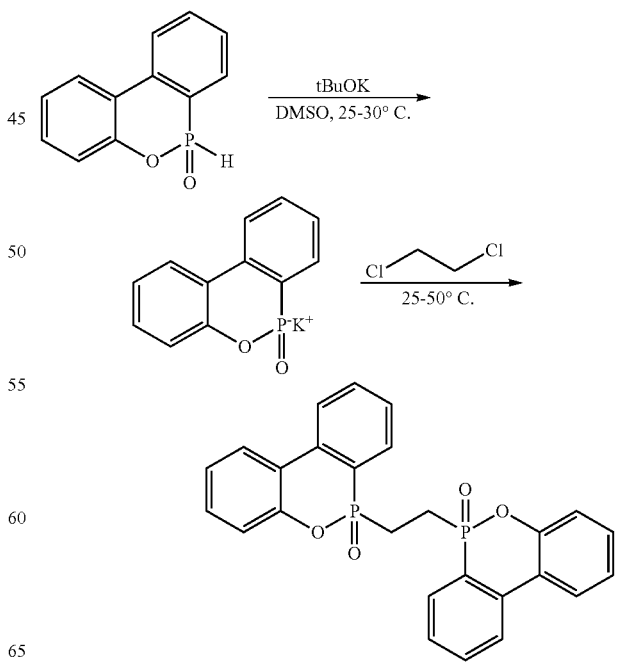

| Component | MW (g/mol) | m.p (° C.) | b.p (° C.) | Physical state | moles | grams | mls | Eq. |
|---|---|---|---|---|---|---|---|---|
| DOPO, CAS # 35948-25-5 TCI America | 216.17 | 119 | — | Solid | 1.96 | 423 | — | 2.1 |
| tBuOK, CAS # 865-47-4, Sigma-Aldrich, St. Louis, MO | 112.21 | 256-258 | — | Solid | 2.05 | 230 | — | 2.2 |
| DMSO, CAS # 67-68-5, Sigma-Aldrich, St. Louis, MO | 78.13 | 16-19 | 189 | Liquid | 21.12 | 1650 | 1500 | 12 |
| Dichloroethane CAS # 75-34-3, Sigma-Aldrich, St. Louis, MO | 98.96 | −35 | 83 | Liquid | 0.93 | 92 | 73 | 1.0 |

A 4-neck 5 L half-jacketed reactor was fitted with an addition funnel, thermocouple, mechanical stirrer and nitrogen flow. The reactor was charged with potassium t-butoxide (tBuOK) (230 g, 2.05 mol) and 1.5 L of anhydrous DMSO as solvent. The mixture was stirred at room temperature until it became a homogenous solution. The solution was cooled to 10° C., and DOPO (423 g, 1.96 mol) was added in nine small portions, keeping the reaction temperature below 30° C. (50-60 g per portion). Dichloroethane (92 g, 0.93 mol) in a 125 ml addition funnel was added to the above solution slowly during 1 h. The reaction was heated to 50° C. for 1 h. The reaction was cooled to 10° C., and water (3 L) was added. The slurry was filtered, and the wet cake was washed with water, acetone and ethyl acetate to give 532 g of crude wet material. The crude material was refluxed in MeCN/ethanol/H2O (5320 ml, v:v:v=1:1:0.5) and cooled to 5° C. slowly. The white solid was filtered through a coarse fitted funnel and dried in a vacuum oven for 8 h at 80° C. to afford a dry white powder (260 g, 68 wt % yield, 99.4 wt % purity, 253-269° C. m.p.). $^{31}$P-NMR(162 MHz, CDCl$_3$): δ 36.45, 36.25 ppm and $^1$H-NMR (400 MHz, CDCl$_3$): δ 7.95 (d, J=8 Hz, 2H, ArH), 7.88 (d, J=8 Hz, 2H, ArH), 7.79-7.69 (m, 4H, ArH), 7.48 (dd, J=7.2 Hz, 14.4 Hz, 2H), 7.37 (dd, J=7.2 Hz, 2H, ArH), 7.29-7.24 (m, 2H, ArH), 7.16 (d, J=12 Hz, 2H, ArH), 2.31 (m, 4H) ppm.

Example 2

6H-Dibenz[c,e][1,2]oxaphosphorin, 6,6'-(1,4-butanediyl)bis-, 6,6'-dioxide

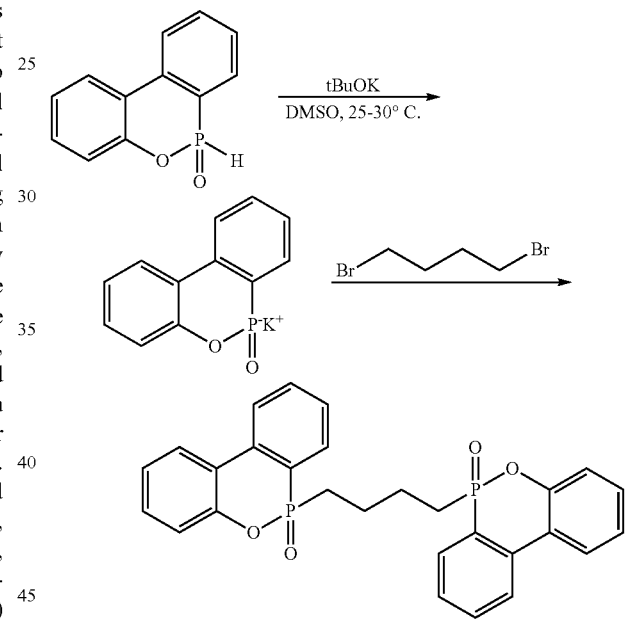

| Component | MW (g/mol) | m.p (° C.) | b.p (° C.) | Physical state | moles | grams | mls | Eq. |
|---|---|---|---|---|---|---|---|---|
| DOPO, CAS # 35948-25-5 TCI America | 216.17 | 119 | — | Solid | 1.68 | 363 | — | 2.1 |
| tBuOK, CAS # 865-47-4, Sigma-Aldrich, St. Louis, MO | 112.21 | 256-258 | — | Solid | 1.76 | 198 | — | 2.2 |
| DMSO, CAS # 67-68-5, Sigma-Aldrich, St. Louis, MO | 78.13 | 16-19 | 189 | Liquid | 14.08 | 1100 | 1000 | 17.6 |
| 1,4-Dibromobutane, CAS # 110-52-1, Sigma-Aldrich, St. Louis, MO | 215.91 | −20 | 63-65° C./ 6 mm Hg | Liquid | 0.8 | 173 | 95 | 1.0 |

A 4-neck 5 L half-jacketed reactor was fitted with a thermocouple, mechanical stirrer, addition funnel and nitrogen flow. The reactor was charged with tBuOK (198 g, 1.76 mol) and 1.0 L of anhydrous DMSO. The mixture was stirred at room temperature until it became a homogenous solution. The solution was cooled to 10° C., and DOPO (363 g, 1.68 mol) was added in six small portions to keep the reaction temperature below 35° C. (60-70 g per portion). After all DOPO was added, 1,4-dibromobutane (173 g, 0.8 mol) was added to the above solution drop-wise slowly during 1 h. The reaction was heated to 30° C. for 1 h. The reaction was cooled to 10° C. and poured on ice. White solid was filtered and washed with acetone and ethyl acetate to give 390 g crude wet material. The crude material (180 g) was refluxed in EtOAc/ethanol (1600 ml, v:v=3:1) and cooled slowly to 0° C. The white solid was filtered through a coarse fitted funnel and dried in a vacuum oven for 8 h at 80° C. to afford a dry white powder (138 g, 81 wt % yield, 176-212° C. m.p.). $^{31}$P-NMR (162 MHz, CDCl$_3$): δ 37.89 ppm; $^1$H-NMR (400 MHz, CDCl$_3$): δ 7.95 (dd, J=8.4 Hz, 1.2 Hz, 2H, ArH), 7.90 (dd, J=8.0 Hz, 1.2 Hz, 2H, ArH), 7.81 (m, 2H, ArH), 7.69 (m, 2H, ArH), 7.50 (m, 2H, ArH), 7.36 (m, 2H, ArH), 7.25 (m, 2H, ArH), 7.16 (m, 2H, ArH), 1.95 (m, 4H), 1.70 (m, 4H).

Example 3

(6H-Dibenz[c,e][1,2]oxaphosphorin, 6,6'-(p-xylene-diyl)bis-, 6,6'-dioxide)

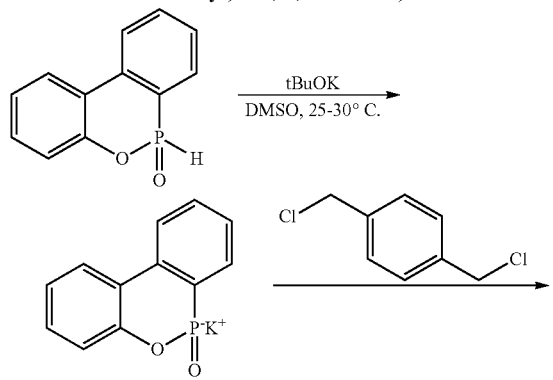

-continued

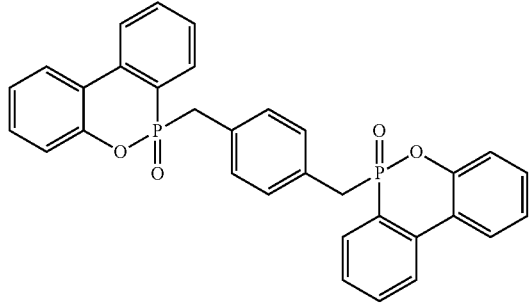

| Component | MW (g/mol) | m.p (° C.) | b.p (° C.) | Physical state | moles | grams | mls | Eq. |
|---|---|---|---|---|---|---|---|---|
| DOPO, CAS # 35948-25-5 TCI America | 216.17 | 119 | — | Solid | 1.68 | 363 | — | 2.1 |
| tBuOK, CAS # 865-47-4, Sigma-Aldrich, St. Louis, MO | 112.21 | 256-258 | — | Solid | 1.76 | 198 | — | 2.2 |
| DMSO, CAS # 67-68-5, Sigma-Aldrich, St. Louis, MO | 78.13 | 16-19 | 189 | Liquid | 14.08 | 1100 | 1000 | 17.6 |
| α,α'-Dichloro-p-xylene, CAS # 623-25-6, Sigma-Aldrich, St. Louis, MO | 175.06 | 98-101 | 254 | Solid | 0.8 | 140 | — | 1.0 |

A 4-neck 4 L half-jacketed reactor was fitted with thermocouple, mechanical stirrer and nitrogen flow. The reactor was charged with tBuOK (198 g, 1.76 mol) and 1.0 L of anhydrous DMSO. The mixture was stirred at room temperature until it became a homogenous solution. The solution was cooled to 10° C., and DOPO (363 g, 1.68 mol) was added in six small portions to keep the reaction temperature below 35° C. (60-70 g per portion). After all DOPO was added, α,α'-Dichloro-p-xylene (140 g, 0.8 mol) was added to the above solution slowly in five small portions (20-30 g per portion). The reaction was heated to 30° C. for 2 h. The reaction was cooled to 10° C., and water (1.5 L) was added. White solid formed at the bottom of the reactor, and the solution was drained. Dichloromethane (2 L) and methanol (1 L) were added to the reactor and heated to reflux (40° C.) until all solids were dissolved. Dichloromethane was distilled, while white solid precipitated. The slurry was cooled to 10° C., and the precipitate was filtered, washed with methanol and dried. The white solid was transferred back to the reactor, and dichloromethane (2 L) and methanol (1 L) were added. The mixture was heated to reflux, and dichloromethane was distilled. The slurry was cooled to 10° C., and the precipitate was filtered and washed with methanol. The wet cake was dried in a vacuum oven at 100° C. for 16 h to afford a dry white powder (138 g, 32% yield, 280-285° C. mp). $^{31}$P-NMR(162 MHz, CDCl$_3$): δ 33.76 ppm; $^1$H-NMR (400 MHz, CDCl$_3$): δ 7.88 (dd, J=8 Hz, 2 Hz, 2H, ArH), 7.83 (dd, J=7.6 Hz, 1.2 Hz, 2H, ArH), 7.66-7.61 (m, 4H, ArH), 7.41-7.34 (m, 4H, ArH), 7.22 (m, 2H, ArH), 7.14 (dd, J=8 Hz, 1.2 Hz, 2H, ArH), 3.30 (m, 4H).

Example 4

Use of 6H-Dibenz[c,e][1,2]oxaphosphorin, 6,6'-(1,4-ethanediyl)bis-, 6,6'-dioxide in epoxy laminate (4% phosphorus content)

In general, stock solutions of advanced resin, curative and promoter are all prepared and stored separately to facilitate experimentation. An 85 wt % phenol epoxy novolac resin solution, DEN® 438-EK85, containing 15 wt % 2-butanone (MEK) was obtained from The Dow Chemical Company. Durite SD-1702 novolac curing agent was obtained from Hexion Corporation. A novolac resin solution was prepared by dissolving 50 wt % SD-1702 in 50 wt % MEK solvent.

The flame retardant of Example 1 (6H-Dibenz[c,e][1,2]oxaphosphorin, 6,6'-(1,4-ethanediyl)bis-, 6,6'-dioxide) containing 13.5 wt % P was ground using a coffee bean grinder to reduce the particle size of the compound to a $d_{50}$ of about 6 µm (bimodal distribution) prior to combining with the polymer. A flame retardant resin mixture containing 4.0 wt % P was prepared by blending 6.31 g of 85 wt % DEN 438 solution, 6.30 g of 50 wt % SD-1702 solution, 3.59 g flame retardant, 0.006 g 2-phenylimidazole promoter (approximately 1.1 mL of a solution containing 0.277 g 2-PhI in 50 mL MEK). The novolac to promoter ratio was about 525. The flame retardant was insoluble in the resin solution until making contact with the hot gel plate, where it dissolved completely at high temperature. About 0.5-1 mL of the resin mixture was added to a hot cure plate (Thermo-electric company) at about 162-164° C. A tongue depressor was split in half lengthwise, and half of the depressor was used to move the resin on the hot plate until stiffness was noted and then lifting the resin with the flat part of the depressor until string formation ceased. The gel time was 4 minutes, 43 seconds, determined by the point where resin "strings" could no longer be pulled from the resin mixture and the epoxy became "tack free".

A larger flame retardant resin varnish containing 4.0 wt % P was prepared in an 8 oz wide-mouth glass jar by adding 63.14 g of 85 wt % DEN 438 solution, 63.00 g of 50 wt % SD-1702 solution, 35.92 g flame retardant and 0.060 g 2-phenylimidazole promoter. An additional 30 g MEK was added to the resin solution. The resin mixture was mixed thoroughly using a high shear mixer stirred at 6,000 rpm for about 15 minutes.

An 11 inch by 11 inch square woven glass fabric (7628 glass with 643 finish from BGF Industries) was cut to size from a large roll and stapled to wood supports (12 inches long, 1 inch wide and 1/16 inch thick) on the top and bottom ends of the fabric. The wood supports contained holes in the corners for inserting paper clips on one end for hanging the fabric in the B-stage oven. The A-stage, or resin varnish, was painted on the front and back of the fabric. Paper clips were unfolded and inserted into the both holes of one wood support. The resin-saturated fabric was hung from aluminum supports in a laboratory fume hood and allowed to drip dry for about one minute before hanging in a pre-heated (to 170° C.) forced air Blue M oven (Lab Safety Supply Inc., a unit of General Signal) for 3 minutes, 50 seconds. The edges of the B-staged prepreg were removed by reducing the sheet dimensions to 10 inch by 10 inch. The sheet was cut into four 5 inch by 5 inch sheets and weighed before stacking the four layers of prepreg between two layers of Pacothane release film (Insulectro Corp.) and two steel plates (1/8 inch thick, 12 inch by 12 inch square dimensions). The laminate was formed in the hot press at 5,000 psig for 1 hour. The resulting laminate was 0.034 inches thick, contained 45 wt % resin and underwent 13 wt % resin overflow during pressing. Five 0.5 inch wide coupons were cut from the laminate using a diamond saw, and the coupon edges were smoothed with sandpaper. The flammability of the coupons were screened by ASTM D3801-06 using an Atlas UL-94 burn chamber, resulting in a V-0 rating with 32 seconds total burn time for the two ignitions on all five coupons.

Example 5

Use of 6H-Dibenz[c,e][1,2]oxaphosphorin, 6,6'-(1,4-ethanediyl)bis-, 6,6'-dioxide in epoxy laminate (3% phosphorus content)

In general, stock solutions of advanced resin, curative and promoter are all prepared and stored separately to facilitate experimentation. An 85 wt % phenol epoxy novolac resin solution, DEN® 438-EK85, containing 15 wt % 2-butanone (MEK) was obtained from The Dow Chemical Company. Durite SD-1702 novolac curing agent was obtained from Hexion Corporation. A novolac resin solution was prepared by dissolving 50 wt % SD-1702 in 50 wt % MEK solvent.

The flame retardant of Example 1 (6H-Dibenz[c,e][1,2]oxaphosphorin, 6,6'-(1,4-ethanediyl)bis-, 6,6'-dioxide) containing 13.5 wt % P was ground using a coffee bean grinder to reduce the particle size of the compound to a $d_{50}$ of about 6 µm (bimodal distribution) prior to combining with the polymer. A flame retardant resin mixture containing 3.0 wt % P was prepared by blending 126.3 g of 85 wt % DEN 438 solution, 126.0 g of 50 wt % SD-1702 solution, 48.8 g flame retardant, 0.12 g 2-phenylimidazole promoter. The novolac to promoter ratio was about 525. The flame retardant was insoluble in the resin solution until making contact with the hot gel plate, where it dissolved completely at high temperature. About 0.5-1 mL of the resin mixture was added to a hot cure plate (Thermo-electric company) at about 162-164° C. A tongue depressor was split in half lengthwise, and half of the depressor was used to move the resin on the hot plate until stiffness was noted and then lifting the resin with the flat part of the depressor until string formation ceased. The gel time was 4 minutes, 22 seconds, determined by the point where resin "strings" could no longer be pulled from the resin mixture and the epoxy became "tack free". An additional 70 g MEK was added to the resin solution. The resin mixture was mixed thoroughly using a high shear mixer stirred at 6,000 rpm for about 15 minutes.

An 11 inch by 11 inch square woven glass fabric (7628 glass with 643 finish from BGF Industries) was cut to size from a large roll and stapled to wood supports (12 inches long, 1 inch wide and 1/16 inch thick) on the top and bottom ends of the fabric. The wood supports contained holes in the corners for inserting paper clips on one end for hanging the fabric in the B-stage oven. The A-stage, or resin varnish, was painted on the front and back of the fabric. Paper clips were unfolded and inserted into the both holes of one wood support. The resin-saturated fabric was hung from aluminum supports in a laboratory fume hood and allowed to drip dry for about one minute before hanging in a pre-heated (to 170° C.) forced air Blue M oven (Lab Safety Supply Inc., a unit of General Signal) for 3 minutes, 30 seconds. The edges of the B-staged prepreg were removed by reducing the sheet dimensions to 10 inch by 10 inch. The sheet was cut into four 5 inch by 5 inch sheets and weighed before stacking the four layers of prepreg between two layers of Pacothane release film (Insulectro Corp.) and two steel plates (1/8 inch thick, 12 inch by 12 inch square dimensions). The laminate was formed in the hot press at 5,000 psig for 1 hour. The resulting laminate was 0.037 inches thick, contained 49 wt % resin and underwent 3 wt % resin overflow during pressing. Five 0.5 inch wide coupons were cut from the laminate using a diamond saw, and the coupon edges were smoothed with sandpaper. The flammability of the coupons were screened by ASTM D3801-06 using an Atlas UL-94 burn chamber, resulting in a V-1 rating with 56 seconds total burn time for the two ignitions on all five coupons. No single burn was greater than 10 seconds.

Example 6

Use of 6H-Dibenz[c,e][1,2]oxaphosphorin, 6,6'-(1,4-butanediyl)bis-, 6,6'-dioxide in epoxy laminate In general, stock solutions of advanced resin, curative and promoter are all prepared and stored separately to facilitate experimentation. An 85 wt % phenol epoxy novolac resin solution, DEN® 438-EK85, containing 15 wt % 2-butanone (MEK) was obtained from The Dow Chemical Company. Durite SD-1702 novolac curing agent was obtained from Hexion Corporation. A novolac resin solution was prepared by dissolving 50 wt % SD-1702 in 50 wt % MEK solvent.

The Flame retardant of Example 2 (6H-Dibenz[c,e][1,2]oxaphosphorin, 6,6'-(1,4-butanediyl)bis-, 6,6'-dioxide) containing 12.7 wt % P was ground using a coffee bean grinder to an average particle size of 29.1 micron ($d_{50}$=23.7 micron). A flame retardant resin mixture containing 4.0 wt % P was prepared by blending 6.31 g of 85 wt % DEN 438 solution, 6.30 g of 50 wt % SD-1702 solution, 3.91 g flame retardant, 0.008 g 2-phenylimidazole promoter (approximately 1.4 mL of a solution containing 0.280 g 2-PhI in 50 mL MEK). The novolac to promoter ratio was about 378. About 0.5-1 mL of the resin mixture was added to a hot cure plate (Thermo-electric company) at about 162-164° C. The flame retardant was insoluble in the resin solution until making contact with the hot gel plate, where it dissolved completely at high temperature. A tongue depressor was split in half lengthwise, and half of the depressor was used to move the resin on the hot plate until stiffness was noted and then lifting the resin with the flat part of the depressor until string formation ceased. The gel time was 5 minutes, 3 seconds, determined by the point where resin "strings" could no longer be pulled from the resin mixture and the epoxy became "tack free".

A larger flame retardant resin varnish containing 4.0 wt % P was prepared in an 8 oz wide-mouth glass jar by adding 63.14 g of 85 wt % DEN 438 solution, 63.00 g of 50 wt % SD-1702 solution, 39.08 g flame retardant and 0.083 g 2-phenylimidazole promoter. An additional 52 g MEK was added to the resin solution. The resin mixture was mixed thoroughly using a high shear mixer stirred at 6,000 rpm for about 15 minutes.

An 11 inch by 11 inch square woven glass fabric (7628 glass with 643 finish from BGF Industries) was cut to size from a large roll and stapled to wood supports (12 inches long, 1 inch wide and 1/16 inch thick) on the top and bottom ends of the fabric. The wood supports contained holes in the corners for inserting paper clips on one end for hanging the fabric in the B-stage oven. The A-stage, or resin varnish, was painted on the front and back of the fabric. Paper clips were unfolded and inserted into the both holes of one wood support. The resin-saturated fabric was hung from aluminum supports in a laboratory fume hood and allowed to drip dry for about one minute before hanging in a pre-heated (to 170° C.) forced air Blue M oven (Lab Safety Supply Inc., a unit of General Signal) for 3 minutes, 40 seconds. The edges of the B-staged prepreg were removed by reducing the sheet dimensions to 10 inch by 10 inch. The sheet was cut into four 5 inch by 5 inch sheets and weighed before stacking the four layers of prepreg between two layers of Pacothane release film (Insulectro Corp.) and two steel plates (1/8 inch thick, 12 inch by 12 inch square dimensions). The laminate was formed in the hot press at 5,000 psig for 1 hour. The resulting laminate was 0.035 inches thick, contained 46 wt % resin and underwent 4 wt % resin overflow during pressing. Five 0.5 inch wide coupons were cut from the laminate using a diamond saw, and the coupon edges were smoothed with sandpaper. The flammability of the coupons were screened by ASTM D3801-06 using an Atlas UL-94 burn chamber, resulting in a V-0 rating with 30 seconds total burn time for the two ignitions on all five coupons.

Example 7

Use of 6H-Dibenz[c,e][1,2]oxaphosphorin, 6,6'-(p-xylenediyl)bis-, 6,6'-dioxide in epoxy laminate In general, stock solutions of advanced resin, curative and promoter are all prepared and stored separately to facilitate experimentation. An 85 wt % phenol epoxy novolac resin solution, DEN® 438-EK85, containing 15 wt % 2-butanone (MEK) was obtained from The Dow Chemical Company. Durite SD-1702 novolac curing agent was obtained from Hexion Corporation. A novolac resin solution was prepared by dissolving 50 wt % SD-1702 in 50 wt % MEK solvent.

The flame retardant of Example 3 (6H-Dibenz[c,e][1,2]oxaphosphorin, 6,6'-(p-xylenediyl)bis-, 6,6'-dioxide) containing 11.6 wt % P was ground using a coffee bean grinder to an average particle size of 16.3 micron ($d_{50}$=15.7 micron). A flame retardant resin mixture containing 4.0 wt % P was prepared by blending 6.31 g of 85 wt % DEN 438 solution, 6.30 g of 50 wt % SD-1702 solution, 4.49 g flame retardant, 0.008 g 2-phenylimidazole promoter (approximately 1.4 mL of a solution containing 0.280 g 2-Ph1 in 50 mL MEK). The novolac to promoter ratio was about 378. The flame retardant was insoluble in the resin solution until making contact with the hot gel plate, where it dissolved completely at high temperature. About 0.5-1 mL of the resin mixture was added to a hot cure plate (Thermo-electric company) at about 162-164° C. A tongue depressor was split in half lengthwise, and half of the depressor was used to move the resin on the hot plate until stiffness was noted and then lifting the resin with the flat part of the depressor until string formation ceased. The gel time was 4 minutes, determined by the point where resin "strings" could no longer be pulled from the resin mixture and the epoxy became "tack free".

A larger flame retardant resin varnish containing 4.0 wt % P was prepared in an 8 oz wide-mouth glass jar by adding 63.14 g of 85 wt % DEN 438 solution, 63.00 g of 50 wt % SD-1702 solution, 44.92 g flame retardant and 0.083 g 2-phenylimidazole promoter. An additional 36 g MEK was added to the resin mixture. The resin mixture was mixed thoroughly using a high shear mixer stirred at 6,000 rpm for about 15 minutes.

An 11 inch by 11 inch square woven glass fabric (7628 glass with 643 finish from BGF Industries) was cut to size from a large roll and stapled to wood supports (12 inches long, 1 inch wide and 1/16 inch thick) on the top and bottom ends of the fabric. The wood supports contained holes in the corners for inserting paper clips on one end for hanging the fabric in the B-stage oven. The A-stage, or resin varnish, was painted on the front and back of the fabric. Paper clips were unfolded and inserted into the both holes of one wood support. The resin-saturated fabric was hung from aluminum supports in a laboratory fume hood and allowed to drip dry for about one minute before hanging in a pre-heated (to 170° C.) forced air Blue M oven (Lab Safety Supply Inc., a unit of General Signal) for 3 minutes. The edges of the B-staged prepreg were removed by reducing the sheet dimensions to 10 inch by 10 inch. The sheet was cut into four 5 inch by 5 inch sheets and weighed before stacking the four layers of prepreg between two layers of Pacothane release film (Insulectro Corp.) and two steel plates (⅛ inch thick, 12 inch by 12 inch square dimensions). The laminate was formed in the hot press at 5,000 psig for 10 minutes. The resulting laminate contained 50 wt % resin. To reduce the wt % resin to the 42-48 wt % range, an additional 15 g MEK solvent was added to the resin mixture. The same procedure as described above was followed to form a laminate that was 0.033 inches thick, contained 46 wt % resin and underwent 13 wt % resin overflow during pressing. Five 0.5 inch wide coupons were cut from the laminate using a diamond saw, and the coupon edges were smoothed with sandpaper. The flammability of the coupons were screened by ASTM D3801-06 using an Atlas UL-94 burn chamber, resulting in a V-0 rating with 43 seconds total burn time for the two ignitions on all five coupons.

COMPARISON EXAMPLE 8

Epoxy Resin Laminate with DOPO (9,10-Dihydro-9-Oxa-10-Phosphaphenantrene-10-oxide)

DOPO is a phosphorus-containing flame retardant compound commonly used to react with epoxy to form laminates in circuit board applications. A 500 mL multi-necked, half-jacketed (and vacuum-jacketed) round-bottom flask was charged with 240.4 g (1.34 equiv.) of DEN 438 Novolac Epoxy resin. Hot (110°) oil from a circulating bath was pumped through the jacket to decrease the viscosity of the resin. Once the resin became fluid, it was stirred at 160 pm with a half-moon Teflon paddle. To the stirred resin was added 0.3 g of an 85% solution of ethyltriphenylphosphonium acetate (catalyst) in methanol. The transfer was completed with approximately 0.5 ml of methanol. The oil was then heated to 120° C. to increase the reactor temperature to 99° C. Two portions, each 90.1 g (0.42 equiv.), of DOPO were added to the reactor. The resulting thick, white slurry was heated by slowly increasing the oil temperature to approximately 180° C. within 2 h. A sample was taken, which had a measured epoxy equivalent weight of 392. The temperature of the reactor was reduced, while simultaneously adding 83 g of 2-butanone. The thick solution was stirred for 30 minutes at 78-80° C. to dissolve the phosphorus-containing epoxy resin. A water-cooled reflux condenser was used to minimize solvent losses. The resultant phosphorus-containing epoxy resin (2.7 wt % P, 428 g) was transferred to a wide-mouth jar.

In general, stock solutions of advanced resin, curative and promoter are all prepared and stored separately to facilitate experimentation. Durite SD-1702 novolac curing agent was obtained from Hexion Corporation. A novolac resin solution was prepared by dissolving 50 wt % SD-1702 in 50 wt % MEK solvent.

Into a 400 ml disposable beaker was accurately weighed 100 g (72.4 wt % resin) of DEN 438 Novolac Epoxy resin solution, previously advanced with DOPO and diluted with 2-butanone in Example 5. To the resin was added 38.4 g of 50 wt % SD-1702 solution and 0.063 g 2-phenylimidozle dissolved in 1.3 g MEK. The novolac to promoter ratio was about 525. The mixture was stirred vigorously to give a light yellow solution. About 0.5-1 mL of the resin solution was added to a hot plate (Thermo-electric Company) at about 162-164° C. A tongue depressor was split in half lengthwise, and half of the depressor was used to move the resin on the hot plate until stiffness was noted and then lifting the resin with the flat part of the depressor until string formation ceased. The gel time was 5 minutes 5 seconds, determined by the point where resin "strings" could no longer be pulled from the resin mixture and the epoxy becomes "tack free".

The resin/curative solution was applied with a paintbrush to an 11"×11" piece of JPS 7628 Fiber Glass Cloth having a CS-718 finish. A 12"×1"×1/16" piece of pine stock is used to support each end of the cloth. Each piece of treated cloth was suspended in a 170° C. forced air Blue M oven (Lab Safety Supply Inc., a unit of General Signal) for a period of time between 3 minutes 45 seconds and 3 minutes 55 seconds ("B-stage") to partially cure the resin. The edges of the B-staged prepreg were removed by reducing the sheet dimensions to 10 inch by 10 inch. The sheet was cut into four 5 inch by 5 inch sheets and weighed before stacking the four layers of prepreg between two layers of Pacothane release film (Insulectro Corp.) and two steel plates (⅛ inch thick, 12 inch by 12 inch square dimensions). The laminate was formed in the 190° C. hot press at 5,000 psig for 1 hour. The resulting laminate thickness was between 0.029 inches and 0.041 inches, containing between 37 wt % resin and 53 wt % resin and underwent between 3% and 26% resin overflow during pressing. The phosphorus content after curing was about 3 wt %. Five 0.5 inch wide coupons were cut from the laminate using a diamond saw, and the coupon edges were smoothed with sandpaper. The flammability of the coupons were screened by ASTM D3801-06 using an Atlas UL-94 burn chamber, resulting in V-0 ratings with between 21 and 48 seconds total burn times for the two ignitions on each set of five coupons.

COMPARISON EXAMPLE 9

Laminate Preparation from DEN 438 Novolac Epoxy Resin with No Flame Retardant

In general, stock solutions of advanced resin, curative and promoter are all prepared and stored separately to facilitate experimentation. An 85 wt % phenol epoxy novolac resin solution, DEN® 438-EK85, containing 15 wt % 2-butanone (MEK) was obtained from The Dow Chemical Company. Durite SD-1702 novolac curing agent was obtained from Hexion Corporation. A novolac resin solution was prepared by dissolving 50 wt % SD-1702 in 50 wt % MEK solvent.

A resin mixture containing no flame retardant was prepared by blending 113.64 g of 85 wt % DEN 438 solution, 113.40 g of 50 wt % SD-1702 solution and 0.0705 g 2-phenylimidazole promoter into a 400 mL disposable plastic beaker. The novolac to promoter ratio was about 804. About 0.5-1 mL of the resin solution was added to a hot cure plate (Thermo-electric company) at about 162-164° C. A tongue depressor was split in half lengthwise, and half of the depressor was used to move the resin on the hot plate until stiffness was noted and then lifting the resin with the flat part of the depressor until string formation ceased. The gel time was 5 minutes, 30 seconds, determined by the point where resin "strings" could no longer be pulled from the resin mixture and the epoxy became "tack free."

A 12 inch by 12 inch square woven glass fabric (JPS 7628 Fiber Glass Cloth having a CS-718 finish) was cut to size from a large roll and stapled to wood supports (12 inches long, 1 inch wide and 1/16 inch thick) on the top and bottom ends of the fabric. The wood supports contained holes in the corners for inserting paper clips on one end for hanging the fabric in the B-stage oven. The A-stage, or resin varnish, was painted on the front and back of the fabric. Paper clips were unfolded and inserted into the both holes of one wood support. The resin-saturated fabric was hung from aluminum supports in a laboratory fume hood and allowed to drip dry for about one minute before hanging in a pre-heated (to 170° C.) forced air Blue M oven (Lab Safety Supply Inc., a unit of General Signal) for a period of time between 4 minutes, 10 seconds and 4 minutes, 30 seconds. The edges of the B-staged prepreg were removed by reducing the sheet dimensions to 10 inch by 10 inch. The sheet was cut into four 5 inch by 5 inch sheets and weighed before stacking the four layers of prepreg between two layers of Pacothane release film (Insulectro Corp.) and two steel plates (⅛ inch thick, 12 inch by 12 inch square dimensions). The laminate was formed in the hot press at 5,000 psig for 1 hour. The resulting laminates were between 0.034 inches and 0.036 inches thick, contained between 44 wt % and 46 wt % resin and underwent between 1 wt % and 18 wt % resin overflow during pressing. Five 0.5 inch wide coupons were cut from the laminate using a diamond saw, and the coupon edges were smoothed with sandpaper. The flammability of the coupons was screened by ASTM D3801-06 using an Atlas UL-94 burn chamber, resulting in burn ratings on all sets of five coupons.

The Laminate Tg measurements were performed similarly to what is described in IPC method IPC-TM-650 (method 2.4.25c), using a 20° C./min temperature rate rise in $N_2$ with the following differences. The isothermal hold temperatures were 200° C. for laminates based on DEN-438 resin, 220° C. for laminates based on NPCN-703 and 250° C. for laminates based on NPCN-703 resin with no flame retardant. The TA Instrument software analyzer was used to determine the glass transition temperature. In some cases a third scan was performed to determine the delta Tg between the first, second and third scans. A hole saw was used to drill out laminate sample disks of a size proportioned to fit inside a standard aluminum DSC pan. The sample edges were gently sanded to for fitting into the pan, and the most in tact surface of the laminate was positioned facing the bottom of the pan. The sample weight (~40-50 mg) was recorded and a sample pan lid added using a plunger press to seal the lid onto the pan. An empty sealed pan was added to the reference platform.

The thermogravimetric analyses (TGA) were performed on a TA Instruments Q500 TGA instrument. The TGA is connected to a PC, which provides user interface and operational system control. The temperature scale was calibrated using certified Curie temperatures of alumel and nickel reference standards. The microbalance was calibrated using certified reference weights. Both of these calibrations were performed according to the instrument manufacturers recommended procedures. The samples contained about 10 mg to 12 mg, which were heated at 10° C./min in under nitrogen from room temperature to 500° C. in platinum sample pans. A raw data file containing the sample weight and temperature data is saved to the PC hard drive during the measurement. After the TGA measurement is finished the raw data file is analyzed for 1%, 2%, 5%, 10% and 50% weight loss temperatures. In addition the weight loss at 500° C. is also calculated.

Comparison of Laminates

Flame retardant and thermal properties of the laminate of Example 4 with 4 wt % phosphorus content and the laminate of Example 5 with 3 wt % phosphorus content were compared to Comparison Example 8 as shown below in Table 1. The flammability (UL-94 ratings) of the laminates was screened by ASTM D3801-06 using an Atlas UL-94 burn chamber (V-O being highest possible rating). The thermogravimetric analysis (TGA) and glass transition temperature (Tg) rate rise was 10° C./min in $N_2$.

TABLE 1

CHARACTERIZATION OF LAMINATES

|  | Inventive Example 4 | Inventive Example 5 | Comparison Example 8 (DOPO) | Comparison Example 9 (No Flame retardant) |
| --- | --- | --- | --- | --- |
| UL-94 | V-0 | V-1 | V-0 | Burn |
| Phosphorus content | 4.0% | 3.0% | 3.0% | 0% |
| Tg (Glass transition temperature | 126-131° C. | 136-140° C. | 117-121° C. | 163-172° C. |
| TGA 5%-wt Loss | 405-411° C. | 405-411° C. | 368-388° C. | 407-421° C. |

Typically, as demonstrated in Comparison Example 8, the introduction of DOPO-based flame retardant compounds results in reduction of Tg, the glass transition temperature of the laminate. Lower Tg can result in less dimensionally stable laminates that are more difficult to process under typical lead-free solder conditions. In addition, the thermal stability, (TGA), is also reduced with DOPO. However, the results demonstrate that Example 5 laminate with 3 wt % phosphorus containing the 6H-Dibenz[c,e][1,2]oxaphosphorin, 6,6'-(1,4-ethanediyl)bis-, 6,6'-dioxide flame retardant of the present invention achieved a V-1 rating without loss of thermal stability (TGA) and also with a significantly higher Tg than the DOPO control. The laminate of Example 4 with 4 wt % phosphorus content has a V-0 rating also with higher Tg and much better TGA temperature stability than the DOPO control.

Example 10

Use of 6H-Dibenz[c,e][1,2]oxaphosphorin, 6,6'-(1,4-ethanediyl)bis-, 6,6'-dioxide in epoxy laminate (3% phosphorus content) with jet milling The procedure outlined in Example 5 was followed except that Jet milling was used to reduce the particle size of the DOPO compound to a $d_{50}$ of about 1.4 μm with a monomodal particle size distribution prior to combining with the epoxy. The flammability of the coupons were screened by ASTM D3801-06 using an Atlas UL-94 burn chamber, resulting in a V-0 rating with 45 seconds total burn time for the two ignitions on all five coupons. No single burn was greater than 10 seconds. The TGA temperature weight loss was 360° C., 381° C. and 404° C. for 1%, 2% and 5% weight loss respectively. This example shows that flammability rating was improved over Example 5 by further reducing the particle size of the DOPO compound prior to mixing with the epoxy.

EXAMPLES 11-22

The procedure used in Example 5 was used to produce laminates in Examples 6 through 17 with the exception that a 60 wt % o-cresol Novolac type epoxy resin (Nan Ya NPCN-703) solution, containing 50 wt % 2-butanone (MEK) was used in place of the phenol epoxy novolac resin and in some examples silica and/or a melamine polyphosphate (Melapur 200 (M-200) from BASF Corporation) were used in the resin mixture. The results are shown in Table 2 below.

TABLE 2

CHARACTERIZATION OF LAMINATES OF EXAMPLES 11 TO 22

| Ex | Wt % Ex. 1 (DOPO) | Total wt % P | M-200 (wt %) | Silica (wt %) | UL-94 Rating | Total burn time | Tg °C. (DSC) | TGA 1% loss | TGA 2% loss | TGA 5% loss |
|---|---|---|---|---|---|---|---|---|---|---|
| 11 | — | — | — | — | Burn | N/A | 198 | 348 | 361 | 382 |
| 12 | 22.2 | 3 | — | — | V-1 | 54 | 156 | 352 | 368 | 396 |
| 13 | 15.6 | 2.1 | — | 30 | V-0 | 41 | 159 | 355 | 375 | 408 |
| 14 | 11.3 | 3 | 11.3 | — | V-0 | 26 | 172 | 332 | 352 | 375 |
| 15 | 10 | 2.68 | 10 | — | V-0 | 41 | 175 | 333 | 349 | 373 |
| 16 | 7 | 1.86 | 7 | 30 | V-0 | 38 | 175 | 343 | 362 | 386 |
| 17 | 9.5 | 2.54 | 9.5 | — | V-0 | 44 | 175 | 336 | 354 | 378 |
| 18 | 6.6 | 1.76 | 6.6 | 30 | V-0 | 19 | 179 | 346 | 363 | 385 |
| 19 | 9 | 2.41 | 9 | — | V-0 | 33 | 177 | 337 | 354 | 376 |
| 20 | 6.3 | 1.67 | 6.3 | 30 | V-1 | 47* | 180 | 339 | 356 | 378 |
| 21 | 8.5 | 2.26 | 8.5 | — | V-1 | 46* | 180 | 340 | 356 | 378 |
| 22 | 8 | 2.14 | 8 | — | V-1 | 100 | 177 | 338 | 355 | 378 |

*One burn greater than 10 seconds.
Total wt % P includes phosphorus from M-200

The results show that the melamine polyphosphate significantly increases the glass transition temperature (Tg), which may be used for high temperature polymer applications. Incorporation of silica allows for a 1.8 wt % P formulation that retains a V-0 rating.

Components referred to by chemical name or formula anywhere in the specification or Claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the Claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

The invention described and claimed herein is not to be limited in scope by the specific examples and embodiments herein disclosed, since these examples and embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended Claims.

The invention claimed is:

1. A flame retardant epoxy composition comprising:
   (i) an epoxy resin;
   (ii) a compound having the following structure:

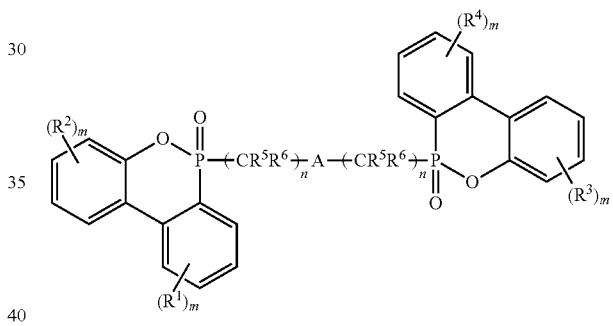

Formula I wherein A is a direct bond, $C_6$-$C_{12}$ aryl, $C_3$-$C_{12}$ cycloalkyl, or a $C_3$-$C_{12}$ cycloalkenyl, wherein said cycloalkyl or cycloalkenyl may be optionally substituted by a $C_1$-$C_6$ alkyl;
each $R^1$, $R^2$, $R^3$ and $R^4$ are independently hydrogen, $C_1$-$C_{15}$ alkyl, $C_6$-$C_{12}$ aryl, $C_7$-$C_{15}$ aralkyl or $C_7$-$C_{15}$ alkaryl; or $R^1$ and $R^2$ or $R^3$ and $R^4$ taken together can form a saturated or unsaturated cyclic ring, wherein said saturated or unsaturated cyclic ring may be optional substituted by a $C_1$-$C_6$ alkyl;
each m is independently 1, 2, 3 or 4
each $R^5$ and $R^6$ are independently hydrogen or a $C_1$-$C_6$ alkyl;
each n is independently 0, 1, 2, 3, 4 or 5;
with the proviso that when A is aryl or a direct bond, n can not be 0.

2. The composition of claim 1, wherein both n subscripts are 1 or 2 and A is a direct bond.

3. The composition of claim 1, wherein both n subscripts are 1 and A is a $C_6$-$C_{12}$ aryl.

4. The compound of claim 2, wherein $R^1$, $R^2$, $R^3$ and $R^4$ are independently hydrogen or a $C_1$-$C_6$ alkyl.

5. The composition of claim 1 wherein the compound of Formula I is 6H-Dibenz[c,e][1,2]oxaphosphorin, 6,6'-(1,4-ethanediyl)bis-, 6,6'-dioxide; 6H-Dibenz[c,e][1,2]oxaphosphorin, 6,6'-(1,4-butanediyl)bis-,6,6'-dioxide; or 6H-Dibenz[c,e][1,2]oxaphosphorin, 6,6'-(p-xylenediyl)bis-,6,6'-dioxide.

6. The composition of claim 5, wherein the compound of Formula I is 6H-Dibenz[c,e][1,2]oxaphosphorin, 6,6'-(1,4-ethanediyl)bis-, 6,6'-dioxide.

7. The composition of claim 1, wherein said epoxy compound is an polyphenol epoxy resin derived from bisphenol A, tetramethylbisphenol A, bisphenol F, bisphenol S, tetrakisphenylolethane, polybenzoxazine, resorcinol, 4,4'-biphenyl or dihydroxynaphthylene; novolac epoxy resin derived from phenol/formaldehyde novolac, cresol/formaldehyde novolac, bisphenol A novolac, biphenyl-, toluene-, xylene-, or mesitylene-modified phenol/formaldehyde novolac or aminotriazine novolac; heterocyclic epoxy resins derived from p-amino phenol or cyanuric acid; and aliphatic epoxy resins derived from 1,4-butanediol, glycerol or dicyclopentadiene; or mixtures thereof.

8. A cured flame retardant epoxyresin comprising reacting the composition of claim 6 with a curing or polymer initiation agent.

9. The resin of claim 8, wherein the organic phosphorous content of the composition is about 0.5 wt % to about 10 wt %, based on the total weight of the resin.

10. The composition of claim 8, further comprising a melamine polyphosphate.

11. The composition of claim 8, further comprising silica.

12. The composition of claim 8, wherein the $d_{50}$ particle of the compound of Formula I is less than about 15 microns.

13. A prepreg comprising an organic or inorganic reinforcing material and the flame retardant epoxy composition of claim 6.

14. A laminate formed from the prepreg of claim 13.

15. A printed wiring board formed from the laminate of claim 14.

* * * * *

UNITED STATES PATENT AND TRADEMARK OFFICE
CERTIFICATE OF CORRECTION

PATENT NO. : 8,536,256 B2  
APPLICATION NO. : 13/319486  
DATED : September 17, 2013  
INVENTOR(S) : Kimberly M. White et al.

Page 1 of 2

It is certified that error appears in the above-identified patent and that said Letters Patent is hereby corrected as shown below:

In the Specification

Column 2, line 1 reads "aryl", and should read - arylene -.
Column 2, line 1 reads "cycloalkyl", and should read - cycloalkylene -.
Column 2, line 2 reads "cycloalkenyl", and should read - cycloalkenylene -.
Column 2, line 2 reads "cycloalkyl", and should read - cycloalkylene -.
Column 2, line 2 reads "cycloalkenyl", and should read - cycloalkenylene -.
Column 2, line 11 reads "aryl", and should read - arylene -.
Column 2, line 37 reads "aryl", and should read - arylene -.
Column 2, line 37 reads "cycloalkyl", and should read - cycloalkylene -.
Column 2, line 38 reads "cycloalkenyl", and should read - cycloalkenylene -.
Column 2, line 38 reads "cycloalkyl", and should read - cycloalkylene -.
Column 2, line 38 reads "cycloalkenyl", and should read - cycloalkenylene -.
Column 2, line 47 reads "aryl", and should read - arylene -.
Column 2, line 51 reads "aryl", and should read - arylene -.
Column 2, line 55 reads "1,4-ethanediyl", and should read - 1,2-ethanediyl -.
Column 7, line 42 reads "aryl", and should read - arylene -.
Column 7, line 42 reads "cycloalkyl", and should read - cycloalkylene -.
Column 7, line 43 reads "cycloalkenyl", and should read - cycloalkenylene -.
Column 7, line 43 reads "cycloalkyl", and should read - cycloalkylene -.
Column 7, line 43 reads "cycloalkenyl", and should read - cycloalkenylene -.
Column 7, line 52 reads "aryl", and should read - arylene -.
Column 8, line 8 reads "aryl", and should read - arylene -.
Column 10, line 37 reads "1,4-ethanediyl", and should read - 1,2-ethanediyl -.
Column 15, line 3 reads "1,4-ethanediyl", and should read - 1,2-ethanediyl -.
Column 15, line 16 reads "1,4-ethanediyl", and should read - 1,2-ethanediyl -.
Column 16, line 10 reads "1,4-ethanediyl", and should read - 1,2-ethanediyl -.
Column 22, line 40 reads "1,4-ethanediyl", and should read - 1,2-ethanediyl -.

Signed and Sealed this  
Third Day of February, 2015

Michelle K. Lee  
*Deputy Director of the United States Patent and Trademark Office*

CERTIFICATE OF CORRECTION (continued)
U.S. Pat. No. 8,536,256 B2

In the Claims

Column 24, line 42 Claim 1 reads "aryl", and should read - arylene -.
Column 24, line 42 Claim 1 reads "cycloalkyl", and should read - cycloalkylene -.
Column 24, line 43 Claim 1 reads "cycloalkenyl", and should read - cycloalkenylene -.
Column 24, line 43 Claim 1 reads "cycloalkyl", and should read - cycloalkylene -.
Column 24, line 43 Claim 1 reads "cycloalkenyl", and should read - cycloalkenylene -.
Column 24, line 53 Claim 1 reads "aryl", and should read - arylene -.
Column 24, line 59 Claim 3 reads "aryl", and should read - arylene -.
Column 24, line 63 Claim 5 reads "1,4-ethanediyl", and should read - 1,2-ethanediyl -.
Column 25, line 2-3 Claim 6 reads "1,4-ethanediyl", and should read - 1,2-ethanediyl -.